United States Patent
Karageozian et al.

(10) Patent No.: US 7,544,671 B2
(45) Date of Patent: Jun. 9, 2009

(54) STABILIZED HYALURONAN PREPARATIONS AND RELATED METHODS

(75) Inventors: Hampar L. Karageozian, San Juan Capistrano, CA (US); John Park, Santa Ana, CA (US)

(73) Assignee: S.K. Pharmaceuticals, Inc., San Juan Capistrano, CA (US)

( * ) Notice: Subject to any disclaimer, the term of this patent is extended or adjusted under 35 U.S.C. 154(b) by 131 days.

(21) Appl. No.: 11/126,075

(22) Filed: May 9, 2005

(65) Prior Publication Data

US 2006/0029571 A1 Feb. 9, 2006

Related U.S. Application Data

(60) Provisional application No. 60/569,407, filed on May 7, 2004.

(51) Int. Cl.
*A01N 43/04* (2006.01)
*A61K 31/715* (2006.01)
(52) U.S. Cl. ............................... 514/54; 514/23; 514/62
(58) Field of Classification Search .................. None
See application file for complete search history.

(56) References Cited

U.S. PATENT DOCUMENTS

| 5,073,545 | A | 12/1991 | Arima et al. | |
|---|---|---|---|---|
| 5,141,741 | A | 8/1992 | Ishida et al. | |
| 6,372,755 | B2 | 4/2002 | Hanamura et al. | |
| 2004/0137079 | A1* | 7/2004 | Cook et al. | 424/662 |
| 2004/0191284 | A1* | 9/2004 | Yu et al. | 424/401 |

OTHER PUBLICATIONS

Steckel et al. International Journal of Pharmaceutics (2003), vol. 257, pp. 181-194.*

* cited by examiner

*Primary Examiner*—Patrick T Lewis
(74) *Attorney, Agent, or Firm*—Robert D. Buyan; Stout, Uxa, Buyam & Mullins

(57) ABSTRACT

Stabilized hyaluronan preparations wherein hyaluronan is combined with a polyglycol, such as polyethylene glycol. Stabilized hyaluronan preparations of this invention may maintain their viscosity and lubricity for extended time periods (e.g., 2 years) without requiring refrigeration or special storage conditions.

28 Claims, No Drawings

STABILIZED HYALURONAN PREPARATIONS AND RELATED METHODS

RELATED APPLICATION

This application claims priority to U.S. Provisional Patent Application No. 60/569,407 filed on May 7, 2004, the entirety of which is expressly incorporated herein by reference.

BACKGROUND OF THE INVENTION

Hyaluronan is a mucopolysaccharide that occurs naturally in the bodies of humans and other animals. The term hyaluronan encompasses hyaluronic acid as well as salts of hyaluronic acid, such as sodium hyaluronate.

Hyaluronan is part of a group of polysaccharides known as glycosaminoglycans. In general, glycosaminoglycans are made up of repeating disaccharide units containing a derivative of an aminosugar. The repeating disaccharide unit of hyaluronan consists of alternating glucuronic acid and N-acetylglucosamine units, which are repeated over and over to form long chains. Each repeating disaccharide unit has one carboxylate group, four hydroxyl groups, and an acetamido group. Hyaluronan differs from the other major glycosaminoglycans in that it does not have sulfate groups. The chemical structure of hyaluronan is as follows:

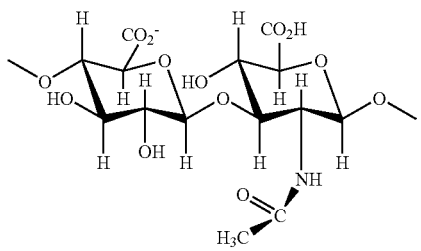

Hyaluronan in the extracellular matrix of various body tissues. In normal physiological states hyaluronan molecules form random coils in the nature of helical ribbons that are stiffened by hydrogen bonds and solvent interactions. The axial hydrogen atoms are relatively non-polar while the equatorial side chains are relatively polar, thereby creating the twisting ribbon structure.

Hyaluronan is synthesized in the body by many types of cells and tends to collect in extracellular spaces where it acts as a scaffold for aggrecan self-assembly, thereby combining with other constituents to form supportive or protective networks around the cells. Hyaluronan is present in many body fluids and tissues and is found in relatively high concentrations in vitreous humor and synovial fluid.

Hyaluronan is highly lubricious, hydrophilic and exhibits unique rheological properties. The unique theology of hyaluronan is believed to be due at least in part to the fact that the hyaluronan polymer coils become entangled with each other at low concentrations and exhibit shear-dependent viscosity at high concentrations. For example, a 1% solution of hyaluronan may exist as a gelatinous mass under ambient conditions but, when compressed, will become less viscous and easily flowable such that it may be injected through a hypodermic needle. Because of this unique rheological behavior, hyaluronan has been referred to as a "pseudo-plastic" material. The hydrophilic nature of hyaluronan is believed to be a function of the fact that hyaluronan forms stiffened helical ribbons as described above. Each such helical ribbon is configured such that it may trap substantial amounts of water (e.g., approximately 1000 times its weight in water).

Hyaluronan has a wide variety of medical and non-medical applications. For example, hyaluronan solutions make excellent lubricants and may allow tissue surfaces to slide over one another. Thus, hyaluronan preparations are sometimes applied to tissues to promote healing and/or to reduce the potential for postoperative adhesion formation. One of its important biological roles is to provide beneficial effects on wound healing in the skin and eyes.

Recently, hyaluronan has been found to enhance corneal epithelial healing and corneal reepithelialization for non-infectious corneal erosion. These beneficial effects can be extended to the management of dry eye syndrome, allergic conjunctivitis, and contact lens wear.

For example, dry eye is a syndrome in which inadequate tear production and inappropriate tear composition causes the cornea and conjunctiva improper wetting. Untreated dry eye can be further deteriorated to produce more severe epithelial erosion, strands of epithelial cells, dry spots on the cornea. These can be complicated further by microbial infection. Thus, an early medical management for the dry eye syndrome would be highly desirable. Such an early treatment of the dryness and irritation of the eye by the use of hyaluronan could be very effective and beneficial medical management of the dry eye.

Additionally, it has been known for a long time that contact lenses which have cellular debris, mucus materials, lipids and proteins from the eye can cause irritation and or infection of the eye. Thus, a biocompatible lubricant, particularly hyaluronan can provide beneficial effects to prevent the deposit from forming in its early stage of deposit formation.

As indicated above, beneficial effects of hyaluronan for the health of the eye are great; however, use of hyaluronan has been rather limited due to its chemical instability losing its viscosity and lubricity in aqueous solution.

SUMMARY IF THE INVENTION

The present invention provides compositions which comprise hyaluronan and at least one polyglycol. The hyaluronan and polyglycol are combined in a ratio, and under condition, which results in a preparation that retains the viscosity and lubricity of the hyaluronan substantially longer than if it had not been combined with the polyglycol. Any suitable hyaluronan (e.g., hyaluronic acid sodium salt) and any suitable polyglycol (e.g., polyethylene glycol) may be used. In some cases, the preparation may include other active or inactive ingredients or reactants including, but not limited to, drugs, cosmetics, preservatives, pH adjusting agents, tonicity adjusting agents, thickening or gelling agents, water, coloring agents, fragrance, etc. The stabilized hyaluronan preparations of this invention may be liquid solutions, gels, creams, or any other useable forms. The stabilized hyaluronan preparations of this invention may be used for a variety of medical and non-medical (e.g., household or industrial) applications, including topical administration to the eye (e.g., to moisturize the eye, treat dry eye, promote corneal healing, facilitate reepithelialization for non-infectious corneal erosion, management of dry eye syndrome, allergic conjunctivitis, and contact lens wear, etc.), topical administration (e.g., to moisturize the skin, to treat dry skin or dermatological disorders), lubrication of body tissues or body orifices, lubrication of devices (e.g., catheters, scopes, instruments, etc.), application to tissues during surgery to deter post-surgical adhesion formation, etc.

Further in accordance with the invention, there are provided methods for manufacturing hyaluronan preparations wherein hyaluronan is combined with a polyglycol. The hyaluronan may be combined with the polyglycol in a ratio and under conditions that result in reaction (e.g., complex formation) between the hyaluronan and the polyglycol such that remains stable for an extended period of time (e.g., 2 years or more) at room temperature.

Further aspects, details and embodiments of the present invention will be understood by those of skill in the art upon reading the detailed description and examples set forth hereinbelow.

DETAILED DESCRIPTION

The following detailed description is intended to describe some, but not necessarily all, examples or embodiments of the invention. No effort has been made to exhaustively describe all possible examples and embodiments of the invention. Thus, the contents of this detailed description shall not limit the scope of the invention in any way.

Applicant has determined that when hyaluronan is combined with a polyglycol the properties of the hyaluronan (e.g., viscosity and lubricity) will be maintained for a prolonged period of time. Thus, polyglycols may be added to or included in various hyaluronan preparations to prolong the shelf stability and usefulness of such preparations.

A polyglycol is defined as a polyhydric alcohol of a monomeric glycol. Polyethylene Glycols (PEGs) are a family of linear, water-soluble polyglycols. PEGs are formed by polymerization of ethylene oxide. The generalized formula for polyethylene glycol is:

$$H-(OCH_2CH_2)_n-OH$$

where "n" is the average number of repeating oxyethylene groups.

Using the methods of the present invention, hyaluronan can be complexed with a PEG to form hyaluronan preparations that remain stable at room temperature for extended periods of time (e.g., 2 years or more) without substantial chemical break down of the hyaluronan and resultant change in viscosity and lubricity.

In preparations of the present invention wherein hyaluronan is combined with a polyglycol (e.g., PEG), the polyglycol may preferably have an average molecular weight in the range of about 200 to about 35,000 and more preferably, in at least some applications, an average molecular weight in the range of about 6000 to about 8000.

Also, in preparations of the present invention wherein hyaluronan is combined with a polyglycol (e.g., PEG), the hyaluronan may preferably have an average molecular weight in the range of about $2 \times 10^3$ to about $5 \times 10^6$ and more preferably, in at least some applications, an average molecular weight in the range of about $2 \times 10^5 - 3 \times 10^6$.

Also, in preparations of the present invention wherein hyaluronan is combined with a polyglycol (e.g., PEG), the weight ratio of hyaluronan to polyglycol may be in the range of from about 0.1:1 to about 10:1 and more preferably in at least some applications such weight ratio of hyaluronan to polyglycol may be in the range of from about 1:2 to about 1:10.

Also, in preparations of the present invention wherein hyaluronan is combined with a polyglycol (e.g., PEG) and any other optional components examples of which are set forth in the formulations shown in Examples 1 and 2 below, the concentration of hyaluronan in the preparation may be in the range of about 0.01% by weight to about 10% by weight.

Also, in preparations of the present invention wherein hyaluronan is combined with a polyglycol (e.g., PEG) and any other optional components examples of which are set forth in the formulations shown in Examples 1 and 2 below, the pH of the preparation may be in the range of from about 5.0 to about 9.5 or more preferably in at least some applications, from about 7.2 to about 7.4. Appropriate acidifying and/or alkaline (e.g., buffering) agents may be added in accordance with procedures will known in the art to adjust the pH of the preparation as need or desired.

Also, in preparations of the present invention wherein hyaluronan is combined with a polyglycol (e.g., PEG) and any other optional components examples of which are set forth in the formulations shown in Examples 1 and 2 below, the tonicity of the preparation may preferably be in the range of about 200 mOsm to about 340 mOsm. Hyperosmolar and/or hypoosmolar agents (e.g., manitol, water, etc.) may be added in accordance with procedures well known in the art to adjust the tonicity of the preparation as need or desired.

EXAMPLE 1

A Stabilized Hyaluronan Preparation

In this example, a liquid hyaluronan preparation is prepared by combining and mixing the components of the following formulation at room temperature:

| | |
|---|---|
| Hyaluronic Acid Sodium Salt | 0.15% |
| Polyethyleneglycol (PEG 8000) | 0.50% |
| Boric Acid | 0.20% |
| Sodium Chloride | 0.58% |
| Postassium Chloride | 0.14% |
| Calcium Chloride Dihydrate | 0.02% |
| Magnesium Chloride Hexahydrate | 0.011% |
| Sodium Chorite/Hydrogen Peroxide | 0.06% |
| Purified Water Q.S | to 100 mL. |

This results in a viscous liquid preparation that is suited for a wide variety of medical or non-medical uses, including use as a lubricant or moisturizing agent, for topical administration to the skin, mucous membranes or eyes, or as a carrier for cosmetics, pharmaceuticals or other agents.

EXAMPLE 2

Stability Comparison

In this example, hyaluronan compositions were prepared under ambient, room temperature conditions according to Formulations I and II, as follows:

| Formula I: | | Formula II: | |
|---|---|---|---|
| Hyaluronic Acid Sodium Salt | 0.15% | Hyaluronic Acid Sodium Salt | 0.15% |
| — | | Polyethyleneglycol (PEG 8000) | 0.5% |
| Boric Acid | 0.2% | Boric Acid | 0.2% |
| Sodium Chloride | 0.58% | Sodium Chloride | 0.58% |

-continued

| Formula I: | | Formula II: | |
|---|---|---|---|
| Postassium Chloride | 0.14% | Postassium Chloride | 0.14% |
| Calcium Chloride Dihydrate | 0.02% | Calcium Chloride Dihydrate | 0.02% |
| Magnesium Chloride Hexahydrate | 0.11% | Magnesium Chloride Hexahydrate | 0.11% |
| Sodium Chorite/ Hydrogen Peroxide | 0.06% | Sodium Chorite/ Hydrogen Peroxide | 0.06% |
| Purified Water Q.S | to 100 mL. | Purified Water Q.S | to 100 mL. |

Both Formulation 1 and Formulation 2 provide a lubricious liquid solution as described in Example 1 above. However, when stored at room temperature, the preparation of Formula I looses substantial viscosity and becomes substantially less lubricious within few weeks. In contrast, the preparation of Formula II remains stable and does not undergo any substantial change in viscosity or lubricity for at least two (2) years.

The invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A composition comprising hyaluronan having an average molecular weight in the range of about $2\times10^3$ to about $5\times10^6$ Daltons in combination with a polyglycol having an average molecular weight in the range of about 6000 to about 8000 Daltons in an amount which prevents the viscosity of the composition from decreasing substantially over a period of at least 2 years when stored in a closed container at room temperature.

2. A composition according to claim 1 wherein the polyglycol comprises polyethylene glycol.

3. A composition according to claim 2 wherein the PEG has an average molecular weight of about 8000 Daltons.

4. A composition according to claim 1 wherein the hyaluronan comprises the sodium salt of hyaluronic acid.

5. A composition according to claim 1 wherein the hyaluronan has an average molecular weight in the range of about $2\times10^5$ to about $3\times10^6$ Daltons.

6. A composition according to claim 1 wherein the weight ratio of hyaluronan to polyglycol is from about 0.1:1 to about 10:1.

7. A composition according to claim 1 wherein the weight ratio of hyaluronan to polyglycol is from about 1:2 to about 1:10.

8. A composition according to claim 1 wherein the concentration of hyaluronan is in the range of from about 0.01% by weight to about 10% by weight.

9. A composition according to claim 1 wherein the composition has a pH in the range of about 5.0 to about 9.5.

10. A composition according to claim 1 wherein the composition has a pH of about 7.2-7.4.

11. A composition according to claim 1 wherein the preparation is a solution having a tonicity in the range of about 200 mOsm to about 340 mOsm.

12. A composition according to claim 1 having the formula:

| | |
|---|---|
| Hyaluronic Acid Sodium Salt | 0.10-6.0% |
| Polyethyleneglycol (PEG 8000) | 0.50-30.0% |
| Boric Acid | 0.20% |
| Sodium Chloride | 0.58% |
| Postassium Chloride | 0.14% |
| Calcium Chloride Dihydrate | 0.02% |
| Magnesium Chloride Hexahydrate | 0.011% |
| Sodium Chorite/Hydrogen Peroxide | 0.06-0.10% |
| Purified Water Q.S | to 100 mL. |

13. A composition according to claim 1 having the formula;

| | |
|---|---|
| Hyaluronic Acid Sodium Salt | about 0.15% |
| Polyethyleneglycol (PEG 8000) | about 0.5% |
| Boric Acid | about 0.2% |
| Sodium Chloride | about 0.58% |
| Postassium Chloride | about 0.14% |
| Calcium Chloride Dihydrate | about 0.02% |
| Magnesium Chloride Hexahydrate | about 0.11% |
| Sodium Chorite/Hydrogen Peroxide | about 0.06% |
| Purified Water Q.S | to 100 mL. |

14. A method for enhancing the stability of a hyaluronan preparation, said method comprising the step of:
   A) combining the hyaluronan having an average molecular weight in the range of about $2\times10^3$ to about $5\times10^6$ with a polyglycol having an average molecular weight of at least 6000 Daltons in an amount which forms a preparation, wherein the viscosity of said preparation will not decrease substantially over a period of at least 2 years when stored in a closed container at room temperature.

15. A method according to claim 14 wherein the desired time period is 2 years.

16. A method according to claim 14 wherein the hyaluronan comprises the sodium salt of hyaluronic acid.

17. A method according to claim 14 wherein the polyclycol comprises PEG.

18. A method according to claim 17 wherein the PEG has an average molecular weight of about 8000 Daltons.

19. A method according to claim 14 wherein Step A comprises combining the hyaluronan and polyglycol in relative amounts and under conditions that cause the hyaluronan to react with the polyglycol to form a hyaluronan-polyglycol complex.

20. A method according to claim 14 wherein the hyaluronan has an average molecular weight in the range of from about $2\times10^5$ to about $3\times10^6$ Daltons.

21. A method according to claim 14 wherein the weight ratio of hyaluronan to polyglycol is from about 1:5 to about 1:10.

22. A method according to claim 14 wherein the weight ratio of hyaluronan to polyglycol is from about 1:5 to about 1:10.

23. A method according to claim 14 wherein the composition has a pH in the range of about 5.0 to about 9.5.

24. A method according to claim 14 further comprising the step of:
B) adjusting the pH of the preparation to a desired pH.

25. A method according to claim 14 further comprising the step of:
B) adjusting the tonicity of the preparation to be in the range of about 200 mOsm to about 340 mOsm.

26. A method according to claim 14 wherein Step A comprises combining:

| | |
|---|---|
| Hyaluronic Acid Sodium Salt | 0.10-6.0% |
| Polyethyleneglycol (PEG 8000) | 0.50-30.0% |
| Boric Acid | 0.20% |
| Sodium Chloride | 0.58% |
| Postassium Chloride | 0.14% |
| Calcium Chloride Dihydrate | 0.02% |
| Magnesium Chloride Hexahydrate | 0.011% |
| Sodium Chorite/Hydrogen Peroxide | 0.06-0.10% |
| Purified Water Q.S | to 100 mL. |

27. A method according to claim 14 wherein Step A comprises combining:

| | |
|---|---|
| Hyaluronic Acid Sodium Salt | about 0.15% |
| Polyethyleneglycol (PEG 8000) | about 0.5% |
| Boric Acid | about 0.2% |
| Sodium Chloride | about 0.58% |
| Postassium Chloride | about 0.14% |
| Calcium Chloride Dihydrate | about 0.02% |
| Magnesium Chloride Hexahydrate | about 0.11% |
| Sodium Chorite/Hydrogen Peroxide | about 0.06% |
| Purified Water Q.S | to 100 mL. |

28. A method according to claim 14 wherein the concentration of hyaluronan is in the range of from about 0.01% by weight to about 10% by weight.

* * * * *

(12) EX PARTE REEXAMINATION CERTIFICATE (8485th)
United States Patent
Karageozian et al.

(10) Number: US 7,544,671 C1
(45) Certificate Issued: Aug. 23, 2011

(54) STABILIZED HYALURONAN PREPARATIONS AND RELATED METHODS

(75) Inventors: Hampar L. Karageozian, San Juan Capistrano, CA (US); John Park, Santa Ana, CA (US)

(73) Assignee: S.K. Pharmaceuticals, Inc., San Juan Capistrano, CA (US)

Reexamination Request:
No. 90/010,823, Jan. 13, 2010

Reexamination Certificate for:
Patent No.: 7,544,671
Issued: Jun. 9, 2009
Appl. No.: 11/126,075
Filed: May 9, 2005

Related U.S. Application Data

(60) Provisional application No. 60/569,407, filed on May 7, 2004.

(51) Int. Cl.
*A01N 43/04* (2006.01)
*A61K 31/715* (2006.01)

(52) U.S. Cl. .............................. 514/54; 514/23; 514/62
(58) Field of Classification Search ........................ None
See application file for complete search history.

(56) References Cited

U.S. PATENT DOCUMENTS

| 4,409,205 A | 10/1983 | Shively |
| 5,510,418 A | 4/1996 | Rhee et al. |
| 5,770,628 A | 6/1998 | Cantoro |

OTHER PUBLICATIONS

Lewis, R.J., Sr., Hawley's Condensed Chemical Dictionary, Fifteenth Edition. Wiley–Interscience, 2007, p. 1011.*

Silver et al., "Physical Properties of Hyaluronic Acid and Hydroxypropylmethylcellulose in Solution: Evaluation of Coating Ability," Journal of Applied Biomaterials, 1994, pp. 89–98, vol. 5, John Wiley & Sons, Inc.

* cited by examiner

*Primary Examiner*—Brenda Brumback

(57) ABSTRACT

Stabilized hyaluronan preparations wherein hyaluronan is combined with a polyglycol, such as polyethylene glycol. Stabilized hyaluronan preparations of this invention may maintain their viscosity and lubricity for extended time periods (e.g., 2 years) without requiring refrigeration or special storage conditions.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-11, 14-25 and 28 are cancelled.
Claims 12, 13, 26 and 27 were not reexamined.

\* \* \* \* \*